United States Patent [19]

Urry

[11] Patent Number: 5,226,292
[45] Date of Patent: Jul. 13, 1993

[54] POLYMERS CAPABLE OF BAROMECHANICAL AND BAROCHEMICAL TRANSDUCTION

[75] Inventor: Dan W. Urry, Birmingham, Ala.

[73] Assignee: UAB Research Foundation, Birmingham, Ala.

[21] Appl. No.: 688,324

[22] Filed: Apr. 22, 1991

[51] Int. Cl.[5] .............................................. F03G 7/00
[52] U.S. Cl. ...................................... 60/721; 530/326; 210/350; 204/403; 623/18
[58] Field of Search ............................ 60/721; 530/326

[56] References Cited

U.S. PATENT DOCUMENTS

| | | | |
|---|---|---|---|
| 4,132,746 | 1/1979 | Urry et al. | 260/857 |
| 4,187,852 | 2/1980 | Urry et al. | 128/334 |
| 4,474,851 | 10/1984 | Urry | 428/373 |
| 4,500,700 | 2/1985 | Urry | 528/328 |
| 4,589,882 | 5/1986 | Urry | 623/11 |
| 4,605,413 | 8/1986 | Urry et al. | 623/11 |
| 5,032,271 | 7/1991 | Urry | 210/350 |

Primary Examiner—Allen M. Ostrager
Attorney, Agent, or Firm—Cooley Godward Castro Huddleson & Tatum

[57] ABSTRACT

A composition that expands against an exerted pressure, which comprises a polymeric material having an inverse temperature transition in the range of liquid water, wherein at least a fraction of the monomers in the polymer contain a hydrophobic group that is present in an amount sufficient to provide PdV/dS for the polymer of at least 0.2° K. The composition can be used in a variety of different application to produce mechanical work or cause chemical changes in a sealed environment by varying the pressure on the composition, with the degree of mechanical or chemical change being controlled by selection of the number, hydrophobicity, and size of the hydrophobic group and the presence or absence of reactive functional groups in the polymer.

8 Claims, 7 Drawing Sheets

Varying the degree of ionization, for example, of a Glu residue shifts the temperature of an inverse temperature transition.

POLYMERS CAPABLE OF BAROMECHANICAL AND BAROCHEMICAL TRANSDUCTION

The Government of the United States has certain rights in this inventions as a result of governmental support.

INTRODUCTION

1. Technical Field

The present invention is directed to the field of bioelastomeric polymers and to uses thereof.

2. Background

Bioelastic polypeptides are a relatively new development that arose in the laboratories of the present inventor and which are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746; 4,187,852; 4,500,700; 4,589,882; and 4,870,055. Bioelastic polymers are also disclosed in related patents directed to polymers containing peptide repeating units that are prepared for other purposes but which can also contain bioelastic segments in the final polymer; see U.S. Pat. No. 4,605,413. A number of other bioelastic materials and methods for their use are described in pending U.S. patent application Ser. Nos. including the following: "Stimulation of Chemotaxis by Chemotactic Peptides," U.S. patent application Ser. No. 355,090, filed May 16, 1989; "Bioelastomer containing Tetra/Pentapeptide Units," U.S. patent application Ser. No. 062,557, filed June 15, 1987; "Reversible Mechanochemical Engines Comprised of Bioelastomers," U.S. patent application Ser. No. 410,018, filed Sept. 20, 1989; "Bioelastomeric Materials Suitable for the Protection of Wound Repair Sites," U.S. Serial No. 184,407, filed Apr. 21, 1988; "Elastomeric Polypeptides as Vascular Prosthetic Materials," U.S. patent application Ser. No. 184,873, filed Apr. 22, 1988; "Polynonapeptide Bioelastomers having an Increased Elastic Modulus," U.S. patent application Ser. No. 314,115, filed Feb. 23, 1989; and "Bioelastomeric Drug Delivery System," U.S. patent application Ser. No. 499,697, filed Mar. 27, 1990. All of these patents and patent applications are herein incorporated by reference, as they describe in detail bioelastomers and/or components thereof that can be used in the compositions and methods of the present invention. These bioelastic materials have been proposed for a number of uses, as indicated by the general subject matter of the applications and patents as set forth above.

The present invention is directed to a new use of bioelastic materials, namely as part of a system in which mechanical or chemical work occurs (or both occur) as a result of a change in pressure on the bioelastic material (or vice versa; i.e., the process is reversible). The process also exists in other polymers having the properties that were discovered originally in the bioelastomers.

In the past, bioelastic compositions have been proposed which respond by contraction or relaxation to changes in chemical environments. See, for example, "Reversible Mechanochemical Engines Comprised of Bioelastomers," U.S. patent application Ser. No. 410,018, filed Sept. 20, 1989, and referenced above. However, this was a system that created or responded to tension forces, not pressures and which had no capability of producing an outward-directed force. By providing compositions and methods by which expansive forces can be created in response to environmental changes or which can use an inward directed pressure to produce mechanical or chemical work, the usefulness of bioelastomers and other polymers is considerably expanded

Relevant Literature

In addition to the patents and patent applications cited above, a number of publications in the scientific literature are relevant to the present invention or are referred to here as evidence of the existence of knowledge in the scientific community. These publications are listed below, and reference is made in the following specification to these literature references by giving the reference number in parentheses at the location where the reference is being cited.

1. Urry, D. W.: *J. Protein Chem.* 7, 1–34 (1988).
2. Urry, D. W.: *J. Protein Chem.* 7, 81–114 (1989).
3. Urry, D. W.: *American Chemical Society, Div. of Polymeric Materials: Sci. and Engineering* 62 (1990).
4. Hollinger, J. O., J. P. Schmitz, R. Yaskovich, M. M. Long, K. U. Prasad, and D. W. Urry: *Calcif. Tissue Int.* 42, 231–236 (1988)
5. Urry, D. W.: *Intl. J. Quantum Chem.: Quantum Biol. Symp.* 15, 235–245 (1988).
6. Edsall, J. T. and H. A. McKenzie: *Adv. Biophys.* 16, 53–183 (1983).
7. Kauzman, W.: *Adv. Protein Chem.* 14, 1–63 (1959).
8. Urry, D. W., C-H Luan, R. Dean Harris, and Karl U. Prasad: *Polymer Preprint Am. Chem. Soc. Div. Polym. Chem.* (1990).
9. Urry, D. W.: *J. Protein Chem.* 3, 403–436 (1984).
10. Chang, D. K., C. M. Venkatachalam, K. U. Prasad, and D. W. Urry; *J. of Biomolecular Structure & Dynamics* 6, 851–858 (1989).
11. Chang, D. K. and D. W. Urry: *J. of Computational Chemistry* 10, 850–855 (1989).
12. Urry, D. W., B. Haynes, H. Zhang, R. D. Harris, and K. U. Prasad: *Proc. Natl. Acad. Sci. USA* 85, 3407–3411 (1988).
13. Urry, D. W., Shao Qing Peng, Larry Hayes, John Jaggard, and R. Dean Harris: *Biopolymers* (1990).
14. Sidman, K. R., W. D. Steber, and A. W. Burg: In *Proceedings, Drug Delivery Systems* (H. L. Gabelnick, Ed.), *DHEW Publication No. (NIH)* 77, -1238, 121–140 (1976).
15. Urry, D. W., D. K. Chang, H. Zhang, and K. U. Prasad: *Biochem. Biophys. Res. Commun.* 153, 832–839 (1988).
16. Robinson, A. B.: *Proc. Nat. Acad. Sci. USA* 71, 885–888 (1974).
17. Urry, D. W.: In *Methods in Enzymology*, (L. W. Cunningham and D. W. Frederiksen, Eds.) *Academic Press, Inc.* 82, 673–716 (1982).
18. Urry, D. W., John Jaggard, R. D. Harris, D. K. Chang, and K. U. Prasad: In *Progress in Biomedical Polymers* (Charles G. Gebelein and Richard L. Dunn, Eds.), *Plenum Publishing Co.* (1990).
19. Urry, D. W., J. Jaggard, K. U. Prasad, T. Parker, and R. D. Harris: *Plenum Press* (1990).
20. Urry, D. W., R. D. Harris, and K. U. Prasad: *J. Am. Chem. Soc.* 110, 3303–3305 (1988).
21. Sciortino, F., M. U. Palma, D. W. Urry, and K. U. Prasad *Biochem. Biophys. Res. Commun.* 157, 1061–1066 (1988).
22. Sciortino, F., D. W. Urry, M. U. Palma, and K. U. Prasad: *Biopolymers* (1990).

23. Pitt, C. G. and A. Schindler, In *Progress in Contraceptive Delivery Systems* (E. Hafez and W. Van Os, Eds.), MTP Press Limited 1, 17–46 (1980).

24. D. W. Urry (1990) *Mat. Res. Soc. Symp.* 174, 243-250, and references therein.

25. D. W. Urry (1990) in *Expanding Frontiers in Polypeptide and Protein Structural Research* (V. Renugopalakrishnan, P. R. Carey, S. G. Huang, A. Storer, and I. C. P. Smith, Eds.) Escom Science Publishers B. V., Leiden, The Netherlands (1991).

26. H. G. Bungenberg de Jong and H. R. Kruyt (1929), *Proc. Kon. Ned. Akad. Wet.* 32, 849.

27. H. G. Bungenberg de Jong and H. R. Kruyt (1930), *Kolloid-Z*, 150, 39.

28. H. G. Bungenberg de Jong, in *Colloid Sci.* (H. R. Kruyt, Ed.) Elsevier, Amsterdam 1949, Vol. 2, Chap. VIII, p. 232.

29. D. W. Urry, R. D. Harris, and K. U. Prasad (1988) *J. Am. Chem. Soc.* 110, 3303-3305.

30. C-H. Luan and D. W. Urry (1990) "Solvent Deuteration Enhancement of Hydrophobicity: DSC Study of the Inverse Temperature Transition of Elastin-based Polypeptides" (submitted for publication).

31. C-H. Luan, J. J. Jaggard, R. D. Harris, and D. W. Urry (1989) *Intl. J. of Qunatum Chem.: Quantum Biol. Symp.* 16, 235-244.

32. D. W. Urry, C-H. Luan, T. M. Parker, D. C. Gowda, K. U. Prasad, M. C. Reid, and A. Safavy (1991) *J. Am. Chem. Soc.*

33. D. W. Urry, T. L. Trapane, and K. U. Prasad (1985) Biopolymers 24, 2345-2356.

SUMMARY OF THE INVENTION

It is an object of the present invention to provide a bioelastomeric system containing a polymer immersed in bulk water that can produce either chemical or mechanical work in response to changes in external pressure.

It is a further object of this invention to provide a bioelastomeric system that can expand against an external force or pressure either in response to that pressure or in response to a change in the chemical environment of the system.

It is still another object of the invention to provide design parameters by which the conditions under which expansion of a composition of the invention can be finely controlled.

These and other objects of the present invention as will hereinafter become more readily apparent have been accomplished by providing a composition capable of expanding against an external pressure, comprising a bioelastic polymer containing elastomeric units selected from the group consisting of bioelastic pentapeptides, tetrapeptides, and nonapeptides, wherein at least a fraction of said elastomeric units contain at least one amino acid residue with a hydrophobic side chain in an amount sufficient to provide PdV/dS for said polymer of at least 0.2° K. The transition characteristics of the elastomers can be controlled by varying the hydrophobicity and size of the side chain (or side chains) and by varying the mole fraction of the hydrophobic units in the overall polymer. The bioelastic polymers as described herein can be used in methods and apparatuses in which mechanical or chemical changes occur as a result of changes in the pressure exerted on the elastomers. Other polymers having an inverse temperature transition in the range of liquid water can also be prepared so as to have the properties described herein.

DESCRIPTION OF THE DRAWINGS

The present invention will be better understood by reference to the following detailed description of the invention and the drawings which form part of the present specification, wherein.

DESCRIPTION OF SPECIFIC EMBODIMENTS

The present invention provides new uses for and new compositions containing bioelastic polypeptides and other polymers that have a key property of such polypeptides, name an inverse temperature transition in the range of liquid water. Polymers that exhibit an inverse temperature transition, which is a phase transition to a condensed state of greater order in water as temperature increases, are typically polymers that contain both polar and hydrophobic regions. These polymers are described in detail below. It has been found that by including relatively large hydrohobic side chains in such polymers that the polymers will respond to pressure in an unexpected way. When pressure is increased on the polymers in an aqueous solution, the polymers expand rather contract This property can now be put to use to achieve mechanical or chemical work, as described below.

Although the invention can be carried out with a number of different polymers, it will be more readily comprehended by concentrating on a particular class of materials having an inverse temperature transition that were the class of polymers originally modified to provide new compositions of the invention.

Bioelastic polypeptides have been previously characterized and described in a number of patents and patent applications described above. These materials contain either tetrapeptide, pentapeptide, or nonapeptide monomers which individually act as elastomeric units within the total polypeptide containing the monomeric units. The elasticity of the monomeric units is believed to be due to a series of $\beta$-turns in the protein's secondary structure, i.e., the conformation of its peptide chain, separated by dynamic (as opposed to rigid) bridging segments suspended between the $\beta$-turns. A $\beta$-turn is characterized by a 10-atom hydrogen-bonded ring of the following formula:

In this formula R₁–R₅ represent the side groups of the respective amino acid residues. The 10-atom ring consists of the carbonyl oxygen of the first amino acid, the amino hydrogen of the fourth amino acid, and the intervening backbone atoms of amino acids two and three. In this monomeric unit as shown, the remaining backbone atoms of the chain (the remainder of amino acid four, amino acid five, and the first part of amino acid one of the next pentameric unit) form the bridging segment that is suspended between adjacent β-turns. Similar structures are present in elastomeric peptide units of other lengths.

This β-turn-containing structure is described in the prior patents and patent applications cited above and need not be described again in detail. Considerable variations in the amino acids that are present at various locations in the repeating units is possible as long as the multiple β-turns with intervening suspended bridging segments are retained in order to preserve elasticity. Furthermore, it is possible to prepare polypeptides in which these monomeric units are interspersed throughout a larger polypeptide that contains peptide segments designed for other purposes. For example, rigid segments can be included to increase the modulus of elasticity or segments having biological activity (such as chemotaxis or cell attachment) can be included for their biological activity.

These elastomeric materials, which include the prototypic poly(Val¹-Pro²-Gly³-Val⁴-Gly⁵) and poly(Val¹-Pro²-Gly³-Gly⁴) molecules as well as numerous analogues, when combined with water form viscoelastic phases which when cross-linked result in soft, compliant, elastomeric matrices (1-3). The VPGVG-based polypentapeptide (and other bioelastomers) has been shown to be biocompatible both before and after cross-linking (4). As implants, such bioelastic polymers are biodegradable, leading to the release of products natural to the body, such as short peptide chains and free amino acids. These polymers, also referred to as elastomeric polypeptide biomaterials or simply bioelastic materials, can be prepared with widely different water compositions, with a wide range of hydrophobicities, with almost any desired shape and porosity, and with a variable degree of cross-linking (either chemically or by irradiation) by selecting different amino acids for the different positions of the monomeric units and by varying the cross-linking process used to form the final product.

Poly(VPGVG), exhibits an inverse temperature transition (24, 25) in which the polypentapeptide folds and assembles into more ordered structures on raising the temperature with formation of a more dense phase called the coacervate phase (26-28). A working model for the molecular structure called a dynamic β-spiral and the supercoiling of several β-spirals to form a twisted filament has been developed based on a wide range of physical and computational methods (24). On γ-irradiation cross-linking an insoluble elastic matrix is formed wherein the molecular folding and assembly is seen as a macroscopic shrinking and extrusion of water from the matrix on raising the temperature. As this thermally driven contraction can be used reversibly to lift weights, the matrix expresses its thermally driven folding as a reversible thermomechanical transduction (24). The temperature for the folding and phase transition can be shifted chemically. By making the polymer more hydrophobic, e.g., Val¹→Ile¹, the transition temperature is lowered; or by making it more hydrophilic, e.g., Val⁴→Ala⁴ or even Val⁴→Glu⁴COOH→ Glu⁴COO⁻, the transition temperature ($T_t$) for coacervate phase formation, is raised. For poly[4(VPGVG),(VPGEG)]where E=Glu, which is equivalent to poly[0.8(VPGVG), 0.2(BPGEG)], it becomes possible in phosphate buffered saline to shift the transition temperature for folding and phase separation from about 20° C. for COOH to about 70° C. for COO⁻, and at the isothermal condition of 37° C. the cross-linked matrix reversibly relaxes on raising the pH to about 7 and contracts on lowering the pH to about 3 (12). In doing so, weights can be lifted; this is chemomechanical transduction. Specifically, $(\partial\mu/\partial f)_{n=\alpha}<0$ where $\mu$ is chemical potential, $f$ is force and $n=\alpha$ indicates constant composition, i.e., in this case a constant degree of ionization (23, 13). The efficiency of this mechanism of chemomechanical transduction appears to be an order of magnitude greater than that mechanism driven by charge-charge repulsion where $(\partial\mu/\partial f)_n<0$ (25). If one recognizes that each chemically induced conformational change to achieve function involves chemomechanical transduction, then it is to be anticipated that proteins utilize this mechanism whenever it is available to achieve chemically induced function.

The preceding may be called polymer-based chemomechanical transduction. It is also possible to change the temperature of the inverse temperature, $T_t$, chemically by changing the solvent composition, and this may be called solvent-based mechanochemical coupling or chemomechanical transduction. Indeed, a small increase in salt (NaCl) concentration can lower the value of $T_t$ and this change can be used to drive chemomechanical transduction (29). Also, deuterium oxide lowers $T_t$ (30); ethylene glycol lowers $T_t$ (31); and urea raises $T_t$ (30). All of these and many other solutes that change the value of $T_t$ can be used to drive chemomechanical transduction.

Phenomenologically, chemomechanical transduction, as exemplified by poly(VPGVG) and its analogs, results from chemical modulation of the temperature of inverse temperature transitions. More descriptively, it is viewed as chemical modulation of the expression of hydrophobicity with both polymer-based and solvent-based means of altering hydrophobic expression. For polymer-based mechanochemical coupling, the driving force appears to arise from structurally-constrained and sufficiently proximal hydrophobic and polar moieties each competing for their uniquely required hydration structures. In other words, there occurs an apolar-polar interaction free energy of hydration which is generally repulsive due, for example, to a polar species achieving improved structuring of hydration shells by destructuring the clathrate-like (caged) water of hydrophobic moieties or conversely, when the cluster of hydrophobic residues becomes more dominant in achieving its cages of water, by limiting the hydration required by the more polar species. This allows that increasing hydrophobicity can cause an increase in carboxyl $pK_a$ by raising the free energy of the more polar species due to inadequate hydration (25). For solvent-based mechanochemical coupling, solutes added to the water solvent interfere with the waters of hydrophobic hydration either by decreasing the activity of water or by directly altering the clathrate-like cage of water.

This application contains the first report on the effects of pressure on $T_t$ for poly(VPGVG) and its more sensitive analogs and describes how to use these systems to exhibit baromechanical transduction. High speed ultracentrifugation was used to develop increased pressures and an analytical ultracentrifuge was used to monitor the transition temperature. Several polymers were synthesized and studied including the homopolypentapeptides poly(GVGVP) and poly(GMGVP) and the complex polypentapeptides poly[0.8(GVGVP), 0.2(GYGVP)], poly[0.8(GVGVP),0.2(GFGVP)] and poly[0.857(GVGVP),0.143(GWGVP)] where M=Met, Y=Tyr, F=Phe, and W=Trp (listed in order of increasing pressure effect), and the results of those and other studies have lead to the present invention.

The present invention thus arose in part with the discovery that incorporation of relatively large hydrophobic side chains in monomeric polypeptide units produces a previously unrecognized property in the resulting overall polymer, namely a sensitivity of the inverse temperature transition of the polymer to external pressure. The new property is not strictly related to hydrophobicity, as were many prior properties, but required the presence of large hydrophobic side chains. Here "large" means preferably larger in volume than an isopropyl group; i.e., larger than 20 cm$^3$/mole. Even larger hydrophobic groups are preferred (e.g., 100, 500, 1000, or even higher volumes as expressed in cm3/mole). The hydrophobic groups are selected to be sufficiently large and to be present in sufficient extent to provide PdV/dS of at least 0.2° K., preferably at least 1° K., more preferably at least 5° K., and most preferably at least 20° K. (where P=pressure, V=volume, and S=entropy). See FIG. 1 and its accompanying discussion for a description of a preferred way in which PdV/dS values can be experimentally determined.

Examples of typical hydrophobic groups include butyl groups and larger hydrocarbons containing 4 or more carbon atoms. There is no particular limit on the upper size of the hydrocarbon other than the ability of the total polymer to undergo the desired inverse temperature transition, which can easily be determined experimentally. Preferred hydrocarbon groups contain 7 to 50 carbons, more preferably 7 to 20 carbons, and typically 7 to 15 carbons. A common substituent comprises a 6-member aromatic ring, such as a phenyl ring. Functional groups can be present on these hydrocarbons as long as the hydrophobic nature of the side chain as a whole is retained. Heteroatoms (e.g., N, S, and O) can also be present in claim and ring structures. Useful hydrophobicity scales for substituents are discussed in more detail below. When polypeptides are prepared, the amino acids phenylalanine, tryptophan, tyrosine, and histidine can be incorporated into the amino acid chains in order to provide the desired large hydrophobic side chains.

Either increasing the size of hydrophobicity of the hydrophobic groups present or increasing their amount (usually expressed as a mole fraction) in a polymer increases the PdV/dS value. However, knowledge of the exact PdV/dS value for a particular polymer is not required in order carry out the present invention, and estimates of whether any given polymer will be likely to have a desirable baromechanical or barochemical response can readily be made by comparison of the amount and type of hydrophobic groups present in a particular polymer. There are no particular upper limits on the size or amount of hydrophobic groups in a polymer of the invention or on the hydrophobicity of the particular substituent as long as the resulting polymer undergoes an inverse temperature transition and has the stated PdV/dS value. However, manufacturing is generally easier if water-soluble polymers (below the transition temperature) are used. Non-water-soluble polymers can be manufactured using organic solvents, but the organic solvent in most cases must be removed and replaced with water after forming the polymer matrix in order to achieve the results described herein.

The invention will be described initially using the model system that was originally helpful in determining the broader aspects of the invention that are later described herein. However, it will be recognized that this initial description is not limiting of the invention, as these examples can readily be modified using the later-described techniques to provide numerous compositions that have the properties discussed herein and which can be used in the methods and apparatuses described later.

The first polymer system showing the baromechanical properties described herein used elastic protein-based polymers of the formula poly[$f_x$(VPGX-G),$f_y$(VPGVG)] where $f_x$ and $f_y$ are mole fractions with $f_x+f_y=1$. As described above, these bioelastomers exhibit inverse temperature transitions in the form of a phase separation in which folding and aggregation of water-soluble polymer chains into more-ordered states of the condensed (coacervate) phase occurs on raising the temperature. This inverse temperature transition, while uncommon in the universe of polymers, is common to the bioelastomers described herein and can readily be detected in other polymers by the simple solution/heating scheme described above. Investigations into the polymers of the formula immediately above in which X=Trp, Phe, or Tyr showed that an increase in pressure caused a substantial increase in the temperature of the transition such that an application of pressure when the polymer is above the transition temperature leads to hydrophobic hydration, unfolding and disaggregation of the polymer, such that the volume of the coacervate phase (or of a cross-linked matrix) increases on increasing pressure. The transition temperature is usually selected to be within 20° C. of the temperature of the medium being pressurized in order to allow pressure effects to occur within a reasonable increase in pressure. By providing $T_t$ closer to the medium temperature (e.g., less than 10° C., preferably less than 5° C., more preferably less than 2° C.), the system is made more sensitive to pressure. Although the inventor does not intend to be limited by the theory of how this expansion takes place, it is believed that water molecules surrounding the aromatic side chains of Trp(W), Phe(F), or Tyr(Y) occupy less volume than water molecules in bulk water surrounding the polymer. The calculated volume change for poly[0.8(GVGVP),0.2(GFGVP)], for example, on going from coacervate phase where hydrophobic associations have largely eliminated waters of hydrophobic hydration to dispersed in water where the hydrophobic moieties are surrounded by water is 80 cm$^3$/mole of mean pentamers, or some 400 cm$^2$/mole of (GFGVP). The results provide the capacity to design materials capable of exhibiting baromechanical transduction.

It should be noted that the location of the "X" residue in the polymer as described above is not critical and was made in these examples principally for ease of synthesis, although some variations in properties do occur with substitution of other amino acid residues in the pentameric elastomer unit. However, the specific location of a side chain in the polymer is not important as long as the bulk properties of the polymer are maintained.

The effect of increased pressures on the temperature of inverse temperature transition, $T_t$, occurs but is quite unremarkable for poly(GVGVP) and poly(GMGVP). On the other hand, the pressure dependence of $T_t$ for polypentapeptides containing aromatic residues is striking. Making comparisons for the same extent of substitution at the same position within poly(Val$^1$-Pro$^2$-Gly$^3$-Val$^4$-Gly$^5$), the magnitude of the change in temperature of the transition, $\Delta T_t$, due to a given increase in pressure is 70 times greater for the Trp$^4$ and 60 times greater for the Phe$^4$ containing polypentapeptides than for the Val$^4$ containing polypentapeptide. Because of the different relative heats for the transitions (32), $L=\Delta H_t$, which are required to obtain an experimental evaluation of the entropies of the transition $\Delta St(=\Delta H_t/T_t)$, the calculated changes in volume for the transition, $\Delta V_t$, are somewhat different. From the slopes in FIG. 1 and with the values of $\Delta S_t$, the values for $\Delta V_t$, are obtained; the changes in volume are 100 times greater for the pentapeptides containing an aromatic residue at position four rather than the Val$^4$ residue. Significantly, the contracted state with respect to the inverse temperature transition for the cross-linked matrix (or of the coacervate) of the polypentapeptide is actually the state of increased volume for the system as a whole (i.e., the polymer and surrounding bulk water). This, of course, means that a gram of water of hydrophobic hydration occupies less volume than a gram of bulk water. The result if a useful effect (i.e., useful in the sense of providing the ability to do useful work) when pressure is applied to a molecular system capable of exhibiting an inverse temperature transition when the molecular system is at a temperature within the transition temperature range and when the composition is pressure sensitive.

The effect of pressure to increase the temperature of an inverse temperature transition has the important result in the transition temperature range of shifting the equilibrium for the polymer toward the swollen state, because this is the state for which the system as a whole and water in particular occupy the smaller volume. The coacervate phase for poly(VPGVG) is 60% water and 40% peptide by weight at 37° C. (33). If, for example, the volume occupied by the 60% water is itself greater than the volume occupied by waters of hydrophobic hydration, then compression of the water bath containing the coacervate phase or of the cross-linked matrix in equilibrium with a water bath will produce a counter pressure due to the shift toward the low temperature, unfolded, swollen state in which an unfolding of the polypentapeptide would bring about exposure of hydrophobic residues with its more densely packed waters of hydrophobic hydration.

Figure 3:
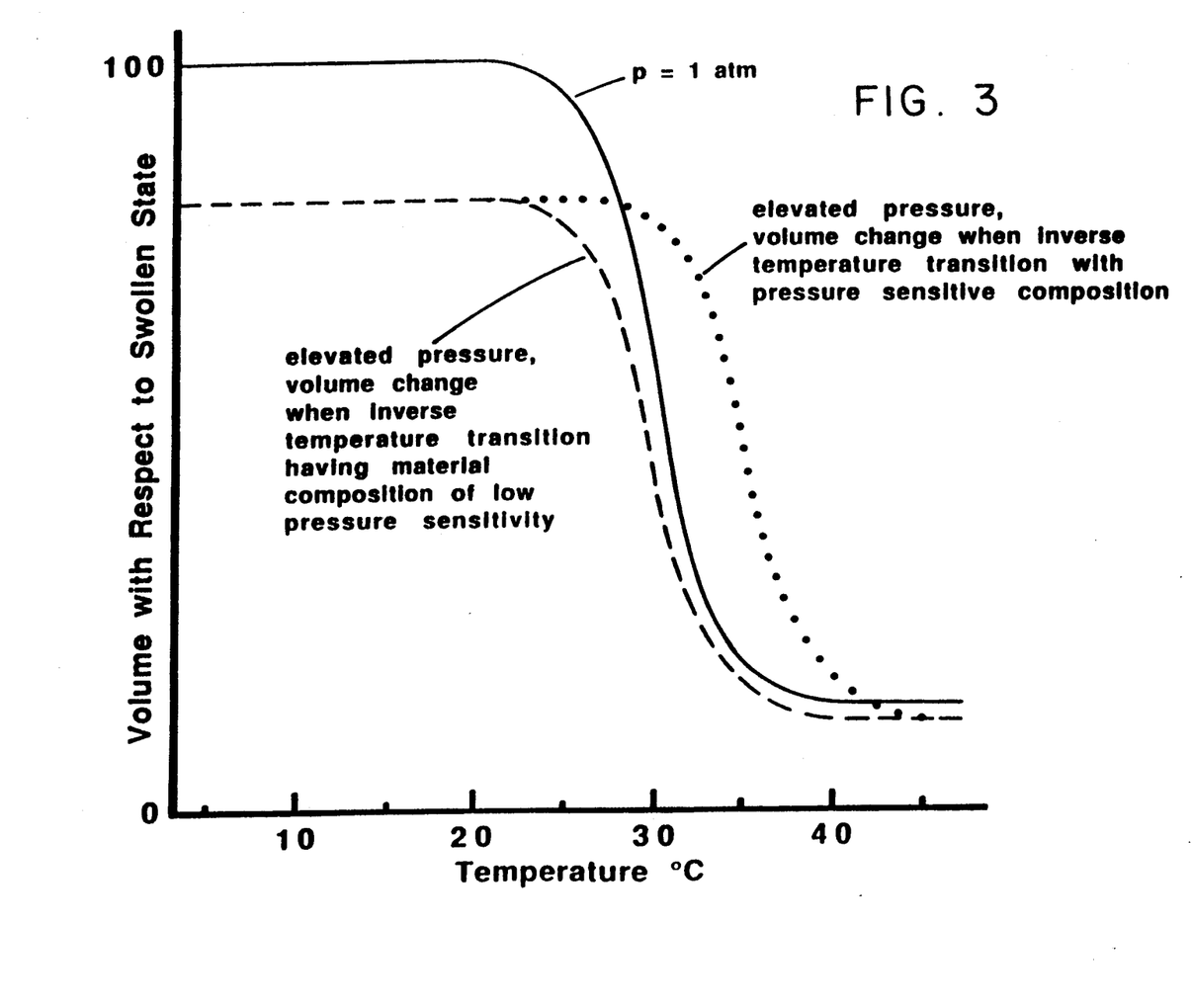
FIG. 3 is a graph showing thermally driven contraction of polymers caused by inverse temperature transitions.

This property is shown in FIG. 3, which contains plots of volume versus temperature. The solid curve is a plot of coacervate (or cross-linked matrix) volume versus temperature for a pressure of one atmosphere. Neglecting for the moment the unique pressure effects on an inverse temperature transition and taking the more swollen state to have a greater coefficient of compression than the contracted state gives the dashed curve for an elevated pressure. Since the effect of increased pressure is to increase the transition temperature, the result of a experimental 4° C. change in $T_t$ (e.g., for the Phe-containing polymer) at 30 atm would be the shift shown by the dotted curve. The effect of pressure is to shift the temperature of the inverse temperature transition in such a way as to counter the effect of applying the pressure.

Figure 1:
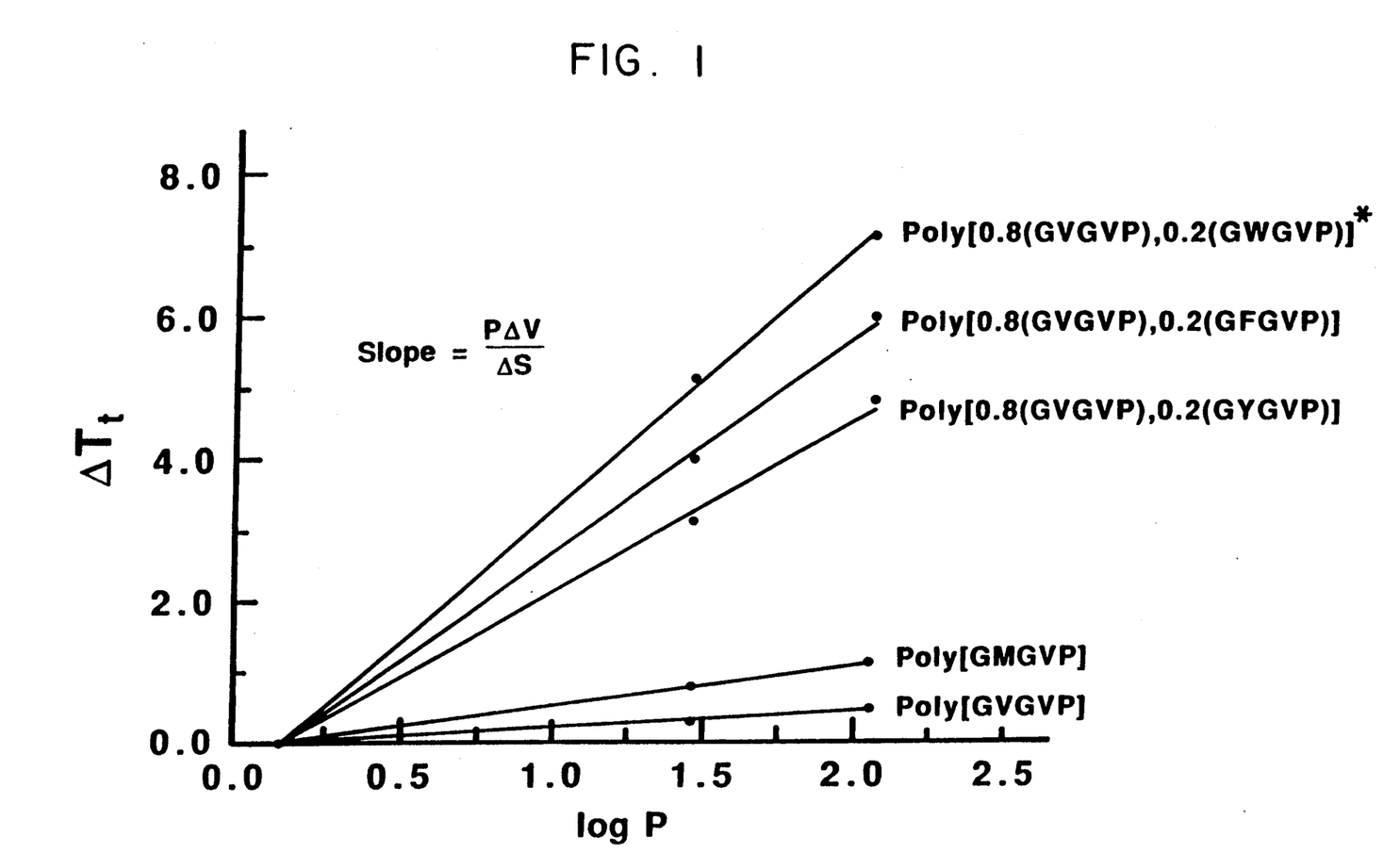
FIG. 1 is a graph showing hyperbaric effects of pressure on the temperature of the inverse temperature transition for selected bioelastomers.
Figure 2A:
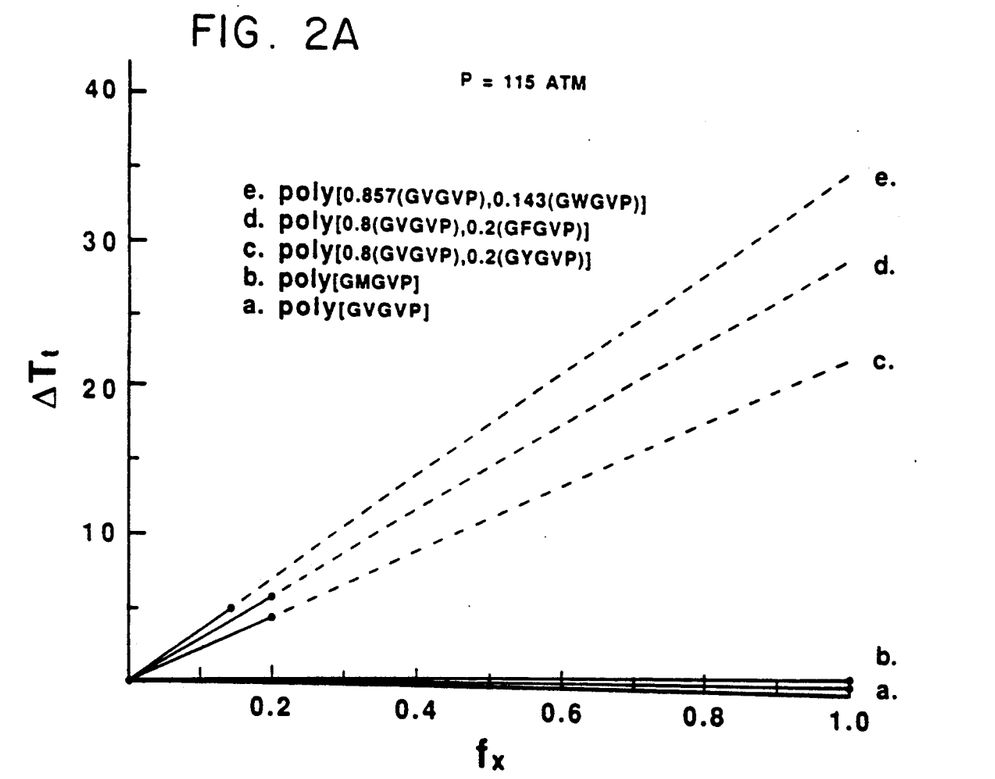
FIGS. 2A and 2B and graphs showing hyperbaric effects of changes in the mole fraction of hydrophobic units in selected bioelastic polymers on the temperature of the inverse temperature transitions of the polymers.
Figure 2B:
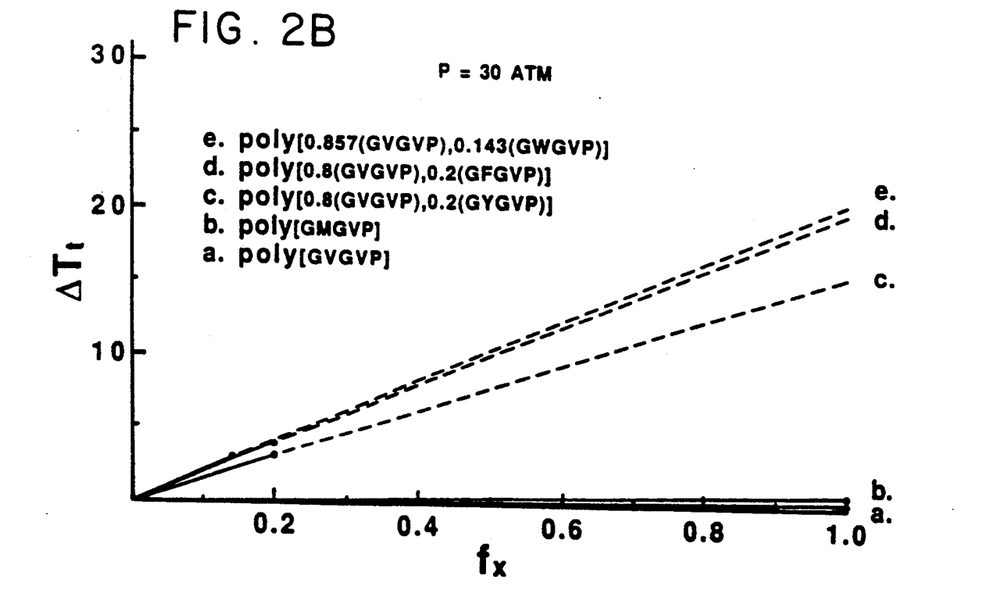

The experimental work demonstrates how pressure-sensitive inverse temperature transitions may be achieved in polypeptides and other proteins as well as in other polymers showing an inverse temperature transition, particularly those having a relatively polar backbone (e.g., polyamides, polyesters). As shown in FIGS. 1 and 2, pressure sensitivity is achieved by having large hydrophobic groups (such as aromatic residues) participate in a folding/unfolding transition. The design would be to have large hydrophobic residues clustered in domains which come into association on folding or which become exposed in unfolding as in a conformational change in which hydrophobic residues are buried in one state and exposed in the other.

Taking these experimental results into consideration, bioelastomers can be rationally designed in order to achieve the desired baromechanical properties described herein. The following discussion describes general selection techniques for achieving the results of the invention with a variety of different bioelastomers.

It is emphasized that the results of balancing hydrophobic (apolar) and polar moieties are not unique to polypeptides but will be applicable to any polymers wherever the appropriate balance can be achieved, for example, for polyesters, polyamides, poly(organophosphazenes), polyacrylamides, polyacrylates, polymethacrylamides, polymethacrylates, etc. Using the relative hydrophobicities and sizes of the side chains, it is possible to construct polymers which will exhibit inverse temperature transitions by a systematic, knowledge-based approach. This approach can be used with natural compounds such as the poly $\beta$-hydroxy alkanoates where there is stereochemical regularity. This can, of course, be achieved with polymers that are degradable as well as with polymers that are not so degradable and also with polymers having greater thermal stability.

The phenomena of inverse temperature transitions in aqueous systems is general and occurs in a number of amphiphilic systems, commonly polymers, that have an appropriate balance and arrangement of apolar and polar moieties. The polar species contribute to the solubility in water at low temperature, a solubility that results in waters of hydrophobic hydration for the apolar moieties. The waters of hydrophobic hydration, often referred to as clathrate or clathrate-like water, have specific thermodynamic properties: an exothermic heat of hydration (a negative $\Delta H$) and a negative entropy of hydration (6,7). On raising the temperature, by means of an endothermic transition (8), the low entropy waters of hydrophobic hydration become bulk water with a significant increase in solvent entropy as the polymers fold and aggregate, optimizing intra- and intermolecular contacts between hydrophobic (apolar) moieties with a somewhat lesser decrease in polymer entropy than increase in solvent entropy. Such polymers, when their transitions occur between 0° and 100° C., can be used to control events in the aqueous environments that occur in biology. However, transitions that occur at other temperatures can also be used in the practice of the present invention, since high pressures on aqueous systems will cause water to remain liquid at temperature outside the normal liquid-water range. Since systems of the invention can operate under 100 atmospheres of pressure or more, the range can be considerably extended.

The polypentapeptide poly(Val$^1$-Pro$^2$-Gly$^3$-Val$^4$-Gly$^5$), also written poly(VPGVG), is a particularly well-balanced polymer for biological utilities as its transition is just complete near 37° C. Below 25° C., it is miscible with water in all proportions where it exhibits a $\beta$-turn (see structural formula above) in which there occur hydrogen bonds between the Val$^1$-CO and the Val$^4$-NH moieties (9). On raising the temperature, the polypentapeptide folds into a loose helix in which the dominant interturn hydrophobic contacts involve the Val$^1$-$\gamma$CH$_3$ moieties in one turn and the Pro$^2$-$\beta$CH$_2$ moiety in the adjacent turn (10). The loose helical structure is called a dynamic $\beta$-spiral and is proposed to be the basis for the entropic elastomeric force exhibited by this material once cross-linked (11). Concomitant with the folding is an assembly of $\beta$-spirals to form a twisted filament which optimizes intermolecular contacts.

When poly(VPGVG) is cross-linked, for example, by 20 Mrads of $\gamma$-irradiation, an elastomeric matrix is formed which is swollen below 25° C. but which on raising the temperature through the transition contracts with the extrusion of sufficient water to decrease the volume to one-tenth and to decrease the length of a strip of matrix to 45% of its swollen length (2). This thermally driven contraction can be used to lift weights that are one thousand times the dry weight of the matrix. This is called thermomechanical transduction. As will be discussed below, any chemical means of reversibility or irreversibility shifting the temperature of the transition can be used, isothermally, to achieve chemomechanical transduction.

Figure 4:
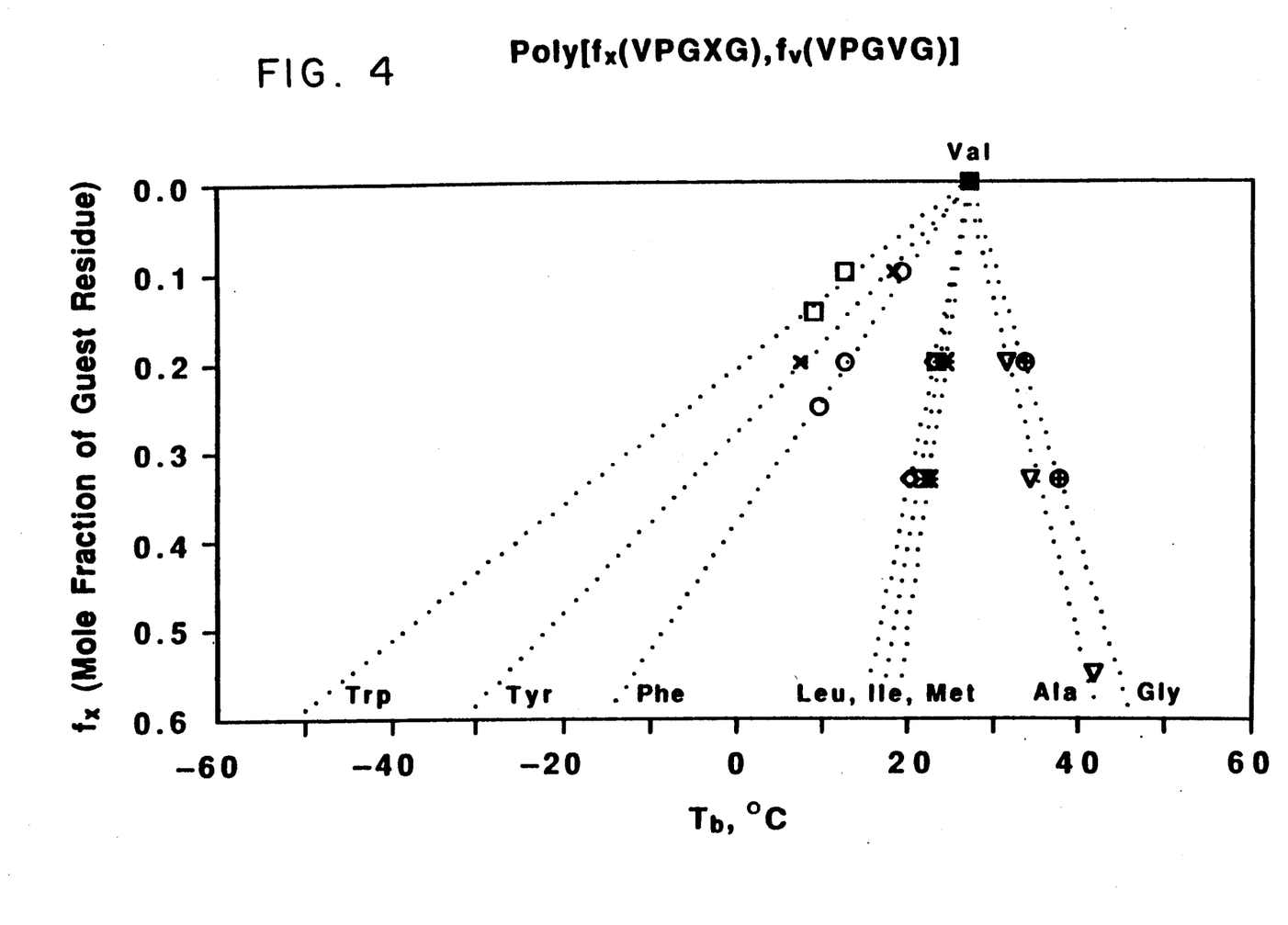
FIG. 4 is a graph showing the relationship of mole fraction of hydrophobic units and hydrophobicity of different hydrophobic units on the temperature of the inverse temperature transition.
Figure 5:
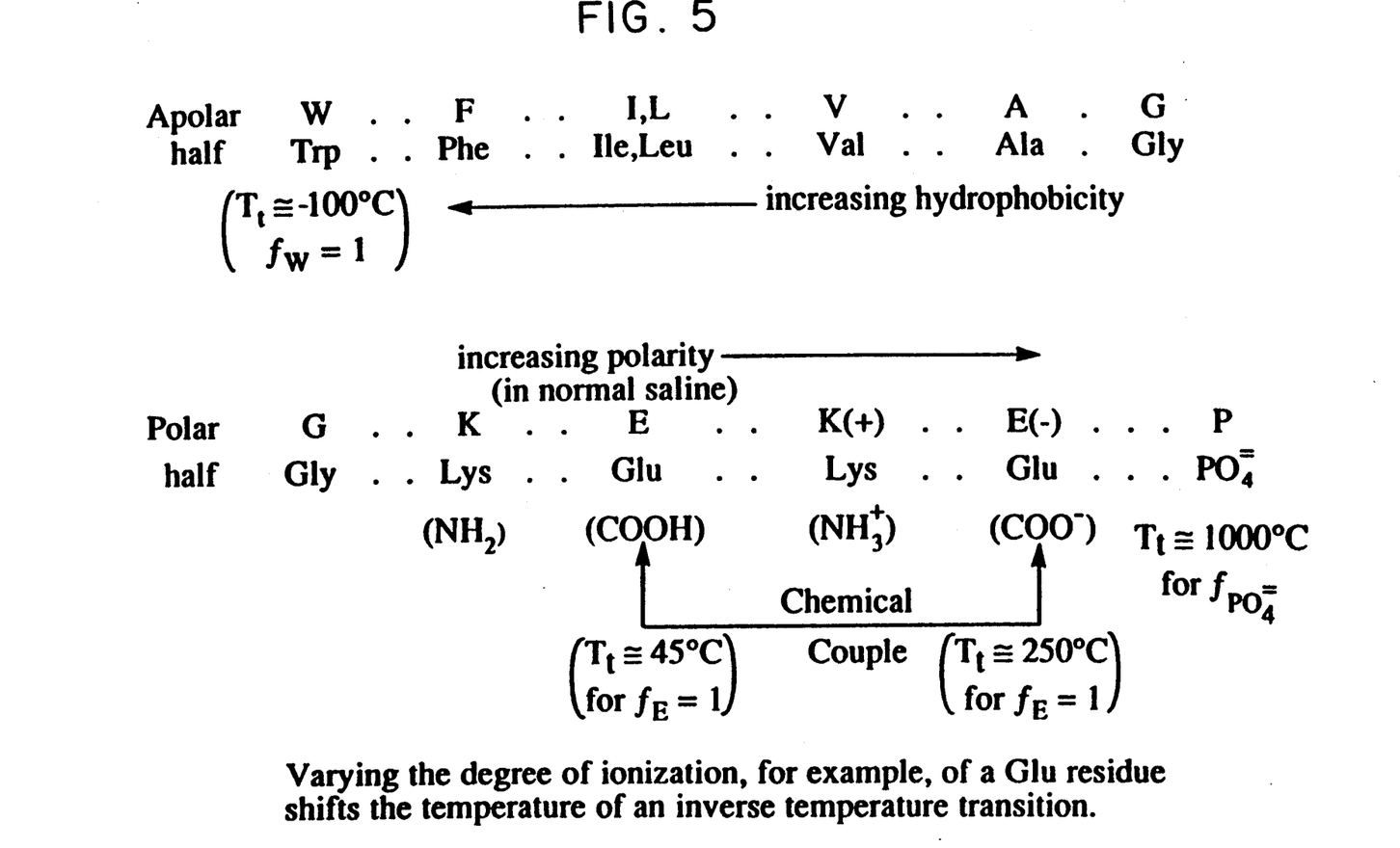
FIG. 5 is a diagram showing a generalized hydrophobicity scale and the change in inverse temperature transition with changes in degree of ionization.

The temperature of the inverse temperature transition of the substituted polypentapeptides described in the following Examples was used to develop a relative hydrophobicity scale as shown in FIG. 4, which contains the apolar side for the natural amino acid residues. The introduction of the polar side is shown in FIG. 5 where protonated/deprotonated chemical couples are introduced which gave rise to polymer-based chemomechanical transduction.

A description of the process of designing bioelastomers specifically to provide an inverse temperature transition at any temperature from 0° C. to 100° C. is described below in detail. The specific examples used below to illustrate this process are mostly examples of elastomeric polypentapeptide matrices. However, it will be apparent that the same considerations can be applied to elastomeric tetrapeptide and nonapeptide matrices and to matrices prepared using these elastomeric units in combination with other polypeptide units as described previously for bioelastic materials.

The temperature of inverse temperature transitions can be changed by changing the hydrophobicity of the polymer. For example, make the polypeptide more hydrophobic, as with poly(Ile$^1$-Pro$^2$-Gly$^3$-Val$^4$-Gly$^5$), where replacing Val$^1$ by Ile$^1$ represents the addition of one CH$_2$ moiety per pentamer, and the temperature of the transition decreases by 20° C. from 30° C. for poly(VPGVG) to 10° C. for poly(IPGVG) (1). Similarly, decreasing the hydrophobicity as by replacing Val$^4$ by Ala$^4$, i.e., removing the two CH$_2$ moieties per pentamer, and the temperature of the transition is raised by some 40° C. to 70° C.

In terms of a generalized hydrophobicity scale, the COOH moiety is more hydrophobic than the COO$^-$ moiety Simply changing the pH of the environment contacting a bioelastomer with free carboxylate groups, the temperature of the transition. The transition temperature can be lowered by decreasing the pH and raised by increasing the pH when a carboxylate group is present (or other group capable of forming an ion upon increasing the pH). If an intermediate temperature is maintained, then a 20 Mrad cross-linked matrix of poly[4(VPGVG),(VPGEG)], that is, a random copolymer in which the two pentameric monomers are present in a 4:1 ratio, where E=Glu, will contract on lowering the pH and relax or swell on raising the pH (12). The temperature of the transition in phosphate buffered saline will shift some 50° C. from about 20° C. at low pH, giving COOH, to nearly 70° C. at neutral pH where all the carboxyls have been converted to carboxylate anions.

For similarly cross-linked poly[4(IPGVG),(IPGEG)], the temperature of the inverse temperature transition shifts from near 10° C. for COOH to over 50° C. for COO$^-$ (5). For this more hydrophobic polypentapeptide, which contains 4 Glu residues per 100 total amino acid residues, it takes twice as many carboxylate anions to shift the transition to 40° C. as for the less hydrophobic polypentapeptide based on the VPGVG monomer. Thus, it is possible to change the conditions of the transition by varying the hydrophobicity of the region surrounding the group that undergoes the chemical change. Since contraction and relaxation of the bulk polymer is dependent on the sum of all local thermodynamic states, sufficient control is possible merely by controlling the average environment of, for example, ionizable groups, such as by changing the percentage of monomers present in a random (or organized) copolymer.

When the pH is lowered (that is, on raising the chemical potential, $\mu$, of the protons present) at the isothermal condition of 37° C., these matrices can exert forces, $f$, sufficient to lift weights that are a thousand times their dry weight. This is chemomechanical transduction, also called mechanochemical coupling. The mechanism by which this occurs is called an hydration-mediated apolar-polar repulsion free energy and is characterized by the equation $(\delta\mu/\delta f)_n < 0$; that is, the change in chemical potential with respect to force at constant matrix composition is a negative quantity (13). Such matrices take up protons on stretching, i.e., stretching exposes more hydrophobic groups to water which makes the COO$^-$ moieties energetically less favored. This is quite distinct from the charge-charge repulsion mechanism for mechanochemical coupling of the type where $(\delta\mu/\delta f)_n < 0$ and where stretching of such matrices causes the release of protons. The hydration-mediated apolar-polar repulsion mechanism appears to be an order of magnitude more efficient in converting chemical work into mechanical work.

It may be emphasized here that any chemical means of changing the mean hydrophobicity of the polymer, such as an acid-base titrable function, dephosphorylation/phosphorylation, reduction/oxidation of a redox couple, etc., can be used to bring about contraction/relaxation. Most transitions will occur on the side chains of certain amino acids, preferably one of the 20 genetically encoded amino acids or a derivative thereof. Especially preferred are changes that can occur to genetically encoded amino acids as a result of contact with a physiological environment. Examples include ionization and neutralization of Glu, Asp, Lys, and His side chains; oxidation of the thio group of Cys (for example to form cystine) or reduction of an oxidized form to Cys; amidation of Glu or Asp; and deamidation of Gln or Asn. It is also possible to attach a moiety containing a functional group that undergoes a transition under conditions different from those attainable for naturally occurring amino acid side chains. For example, a sulfate ester of Ser can be prepared in which sulfate ionizations will occur at a pH outside the range experienced by carboxylate groups. A change in the oxidation state of NAD, a flavin, or a quinone attached to an amino acid by reaction of a functional group in the modifying moiety and a functional group in an amino acid side chain is also effective. A specific example of such a modified amino acid residue is a riboflavin attached to the carboxylate group of a Glu or Asp residue through formation of an ester linkage. Another example would be a heme moiety covalently bonded to the side chain of an amino acid. For example, protoporphyin IX can be attached to the amino group of Lys through one of its own carboxylate groups. Heme A (from the cytochromes of class A) could be attached in a similar manner. Change in the oxidation state of, or coordination of a ligand with, the iron atom in a heme attached to an amino acid side chain can also be used to trigger the desired transition.

It is also possible to exert fine control over the transition from a relaxed to a contracted state (or vice versa) by controlling the average environment in which the various functional groups undergoing transition are located. For example, the hydrophobicity of the overall polymer (and therefore the average hydrophobicity of functional groups present in the polymer) can be modified by changing the ratio of different types of monomeric unit, as previously exemplified. These can be monomeric units containing the functional group undergoing the transition or other monomeric units present in the polymer. For example, if the basic monomeric unit is VPGVG and the unit undergoing transition is VPGKG, where K is a lysine residue, either the ratio of VPGVG unit to VPGKG units can be varied or a different structural unit, such as IPGVG, can be included in varied amounts until the appropriate transitions temperature is achieved.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification, and measuring the transition temperature as described herein and in the cited patents and patent applications. Preferably, however, one uses tables of relative hydrophobicity of amino acid residues (either naturally occurring or modified) to compute the transition temperature without experimentation. For example, see Y. Nozaki and C. Tanford, *J. Biol. Chem.* (1971) 246:2211–2217, or H. B. Bull and K. Breese, *Archives Biochem. Biophys.* (1974) 161:665–670, for particularly useful compilations of hydrophobicity data. Some 30 different hydrophobicity scales exist, with the hydrophobicity scales that show tryptophan (Trp) as the most hydrophobic (or at least one of the most hydrophobic) residues being more appropriate for the practice of the present invention. For example, a rough estimate can be obtained of the likely transition temperature by summing the mean hydrophobicities of the individual amino acid residues in the monomeric units of the polymer and comparing the result to the sum obtained for polymers having known transition temperatures.

More accurate values can be calculated for any given polymer by measuring transition temperatures for a series of related polymers in which only one component is varied. For example, polymers that mostly contain VPGVG monomers with varying amounts of VPGKG monomers (e.g., 2%, 4%, and 8% K) can be prepared and tested for transition temperatures. The test merely consists of preparing the polymer in uncrosslinked form, dissolving the polymer in water, and raising the temperature of the solution until turbidity appears, which indicates the precipitation of polymer from solution. If the transition temperatures are plotted versus the fraction of VPGKG monomer in the polymer, a straight line is obtained, and the fraction of VPGKG necessary for any other desired temperature (within the limits indicated by 0% to 100% of the VPGKG monomer) can be obtained directly from the graph. When this technique is combined with the rough estimating ability of hydrophobicity summing as described above, any desired transition temperature in the range of liquid water can be obtained.

Bioelastomeric materials provide a chemically modulatable polymer system as part of which there can be a controlled rate of presentation of more polar species such as the carboxylate anion. By the mechanism described above where $(\delta\mu/\delta f)_n < 0$, the pKa of a carboxyl moiety in a polymeric chain can be increased by increasingly vicinal hydrophobicity (13, 15).

Figure 6:
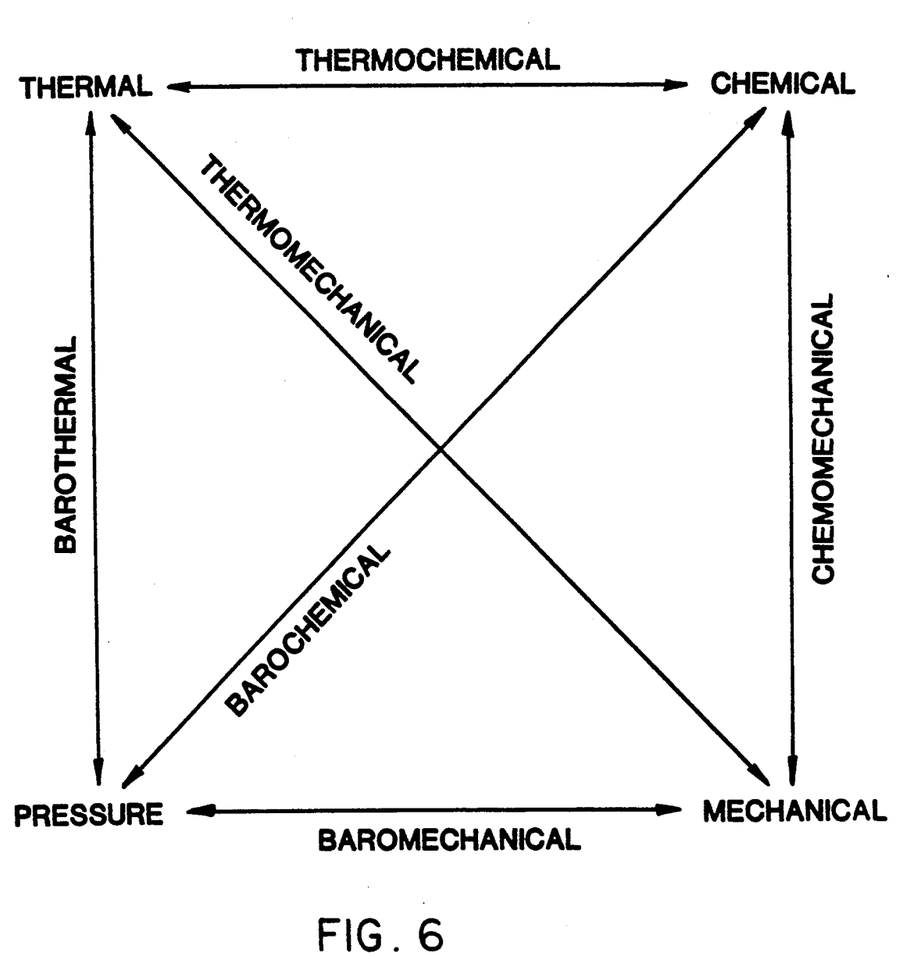
FIG. 6 is a diagram showing thermal, chemical, pressure, and mechanical free energy transductions in polymers of the invention.

Although the discussion above is general to the phenomanon of controlling inverse temperature transitions in bioelastomers, regardless of whether those materials have the baromechanical and barochemical properties of the invention, it will be recognized that the same discussion is relevant to varying the inverse temperature transition of compositions of the invention. As previously discussed, polymers of the invention merely incorporate hydrophobic side chains of a sufficient number and size to provide the desired pressure-sensitive effects. Providing a polymer with the pressure-sensitive effects of the invention, however, does not eliminate the other properties of these polymers. Accordingly, it is possible to achieve the various mechanochemical and thermochemical properties that have been previously described in, for example, bioelastic materials by providing a polymer that contains functional groups in addition to those required for pressure sensitivity. As illustrated in FIG. 6, selection of chemically sensitive side chains or large hydrophobic side chains (for pressure sensitivity) allow all 6 of the potential free energy transductions between chemical, thermal, pressure, and mechanical energy to occur using compositions of the invention. A polymer will have the inherent thermal and mechanical properties if it merely has the polymer backbone and the required inverse temperature transition. By providing large hydrophobic side chains, pressure capabilities will be provided, while providing side chains with chemical functionality will allow chemical interactions to take place.

The pressure-resisting materials of the invention can be used in a variety of different methods, apparatuses that perform work, and devices that resist pressure or cushion against shock. It will be apparent that useful mechanical and/or chemical work can be obtained from the expansions and contractions of the compositions of the invention with changes in pressure and that such work can be used in a variety of situations, particularly in sealed systems that operate under existing high pressures and that therefore are difficult to mechanically manipulate from outside the system. The follow examples of methods, apparatuses, and devices are only a few of the many possible variations.

One method of the invention produces mechanical work by changing pressure on a composition of the invention as described above. The composition, usually polymer in an aqueous environment surrounded by bulk water so that water can move into and out of the polymer as transitions occur, is constrained so that expansion and/or contraction of the polymer produces mechanical work. One manner of providing the desired pressure change on the composition is to provide the composition in a aqueous environment and to change the pressure that the water exerts on the polymer. The change can be an increase or decrease in pressure, depending of the type of constraint on the polymer (i.e., whether it is being constrained against expansion or contraction).

Figure 7:
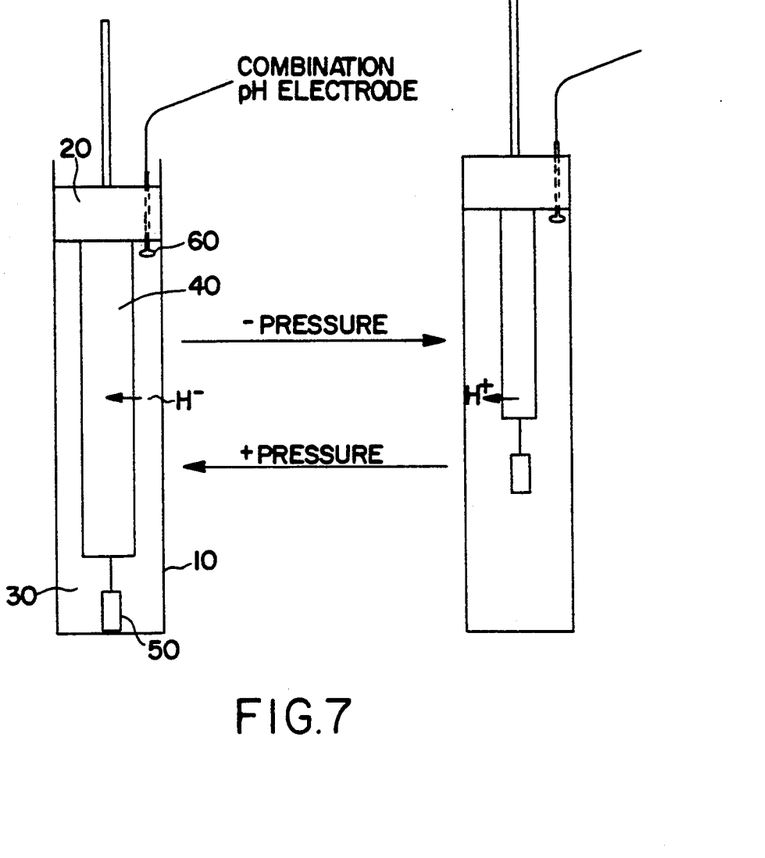
FIG. 7 is a schematic diagram of an apparatus of the invention in which either mechanical work is achieved by a change in pressure or a change in pressure can cause chemical work detectable through a pH meter.

As an example, an apparatus for producing mechanical work can be prepared that contains a polymer or other material of the invention that is constrained so that expansion or contraction of the polymer will produce mechanical work. When the pressure on the polymer is changed, the polymer will expand or contract to produce the desired work. An example of a pressurized system is a cylinder (10) with a moveable piston (20) that encloses an aqueous medium (30) containing a composition of the invention (40). See, for example, FIG. 7. The composition is prepared in the form of a strip, with one end of the strip being attached to a fixed location in the cylinder (illustrated by attachment to piston (20) and the other end being attached to the object being moved. This object is illustrated by a suspended weight (50) in FIG. 7, but could be a lever, switch, or other mechanical operation. Increasing the pressure on the piston (and therefore on the enclosed aqueous medium and composition) will cause the weight suspended in the cylinder to be lowered (i.e., moving from the right panel of FIG. 7 to the left panel). Decreasing the pressure (moving from the left panel to the right panel) will cause the weight to be raised as the supporting strip contracts.

Figure 8:
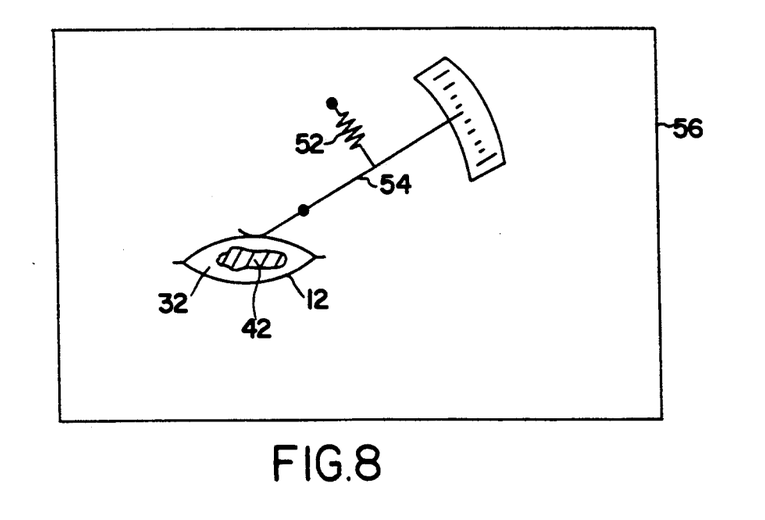
FIG. 8 is a schematic diagram of a pressure meter that operates using a composition of the invention.

An alternative apparatus for producing useful work uses a deformable sheath 12 (e.g., a sealed flexible metal container) surrounding an aqueous medium 32 containing a composition of the invention 42. Changing the pressure on the sheath causes the internal fluid to contract or expand (rather than merely move to another location as in a simple hydrostatic system), allowing motion to be imparted to an object contacting the sheath so that it moves through a distance against an opposing force (such as a spring 52). The object can be, for example, a lever 54 that functions as the movement arm of a pressure gauge 56, either for measuring atmospheric pressure or (more commonly) depth under the surface of water. The expansion and contraction are greater than would occur for a simple water solution, providing for a more sensitive pressure meter. The same system can also function as a thermometer if pressure is constant, as thermal effects of expansion and contraction of water are also enhanced by enclosing a composition of the invention in the aqueous medium.

When functional groups capable of undergoing reversible chemical change are included in the compositions, chemical changes can be caused to occur in sealed systems merely by changing the pressure on the system. For example, if the chemical change is protonation, a pH change can be caused in the environment surrounding a composition of the invention by applying pressure to the environment; application of the pressure causes a change in the pKa of the composition and a resulting change of pH in the environment. This method can readily be embodied in an apparatus. For example, the previously described cylinder and piston, when it encloses an aqueous medium containing a composition of the invention that contains ionizable functional groups, will undergo a change of pH in the aqueous medium merely by changing the pressure on the piston without requiring introduction of reagents into the medium.

This pH-modifying system can be used in reverse to provide mechanical work. A composition of the invention is located in an aqueous environment and the composition is constrained so that expansion (or contraction if desired) of the composition will produce mechanical work; by allowing or causing the pH in the environment to change, the change in pH causes a change in protonation of the composition and a resulting expansion (or contraction) of the composition, thereby producing the desired mechanical work. For example, a stirrer can be powered in a sealed chemical system that is undergoing a pH change as a result of chemical reaction by using the expansion (or contraction) of a strip of inventive composition to power the stirrer through any system than converts linear motion to rotary motion.

In an alternative embodiment, pressure can be measured through changes in pH of the aqueous medium suffounding a composition of the invention as the aqueous medium undergoes pressure changes. Referring again to FIG. 7, cylinder 10 and piston 20 can be fitted with pH electrode 60 inserted through the wall of the cylinder or piston. A composition of the invention is enclosed in this container along with bulk water. The mechanochemical constraint, as exemplified by weight 50, is not required in this embodiment. As the pressure on the piston changes and either compresses or expands the water/composition mixture, pKa changes in the composition will cause pH changes in the surrounding water. It is merely necessary to have the scale of the pH meter calibrated in atmospheres of pressure to have the system provide a direct pressure reading at a remote location.

Compositions of the invention are also useful in situations where resistance to shock is desired, since they tend to resist contraction when subjected to a normally compressive force (i.e, an increase in pressure). One useful application for the composition of the invention is therefore as replacements for natural articular cartilage. An artificial articular cartilage can be prepared which comprises a composition of the invention shaped to replace at least a portion of a natural articular cartridge in an articulated joint of a vertebrate, such as a human or other mammal. The compositions can also be used to form weight-bearing surfaces of artificial joints, in the same manner that teflon surfaces are now used on a steel joint prosthesis. The composition of the invention will provide greater resistance to shock as shocks to the joint will produce water structural changes that will resist compression and slow the flow of water out of the water-impregnated composition. Particularly preferred for this purpose are materials based on elastomeric pentapeptide, tetrapeptide, and nonapeptide monomers as described herein, as these material have already been demonstrated to be biocompatible. See the various patents and patent applications listed above dealing with biocompatible uses of these materials and the formation of these materials into prosthetic devices. Although these prior patents and applications have not been concerned with cartilage or joint replacements, they provide considerable guidance on biocompatibility and on manufacturing of bioelastomers as structural and surface features of prosthetic devices.

The invention now being generally described, the same will be better understood by reference to the following examples, which are provided for purposes of illustration only and are not to be considered limiting of the invention unless so specified.

EXAMPLE

MATERIALS AND METHODS

The syntheses of poly(GVGVP), which can be considered identical to poly(VPGVG) when the degree of polymerization is large as in this case (n>120), has been reported previously (11, 12). The choice of the pentamer permutation ending in Pro for polymerization, i.e., (GVGVP), arises from the higher molecular weights so obtained (11) whereas for description of conformation the pentamer (VPGVG) is preferred because of a hydrogen bond between the $Val^1$ C-O preceding the Pro residue and the immediately following $Val^4$ NH between the two Gly residues (1). The related polymers of the invention poly(GMGVP), poly[0.8(GVGVP), 0.2(GYGVP)], poly[0.8(GVGVP),0.2(GFGVP)] and poly[0.857(GVGVP),0.143(GWGVP)] were prepared in a similar fashion. The verification of the syntheses was provided by proton and carbon-13 nuclear magnetic resonance analysis. The general formula is poly-$[f_v(GVGVP), f_x(GXGVP)]$ where $f_x$ and $f_v = 1$ and therefore $f_x$ and $f_v$ are the mole fractions of pentamers in the polypentapeptide.

A Beckman Model E Analytical Ultracentrifuge was used to generate the pressure. This instrument can drive rotors to speeds of 68,000 rpm and can generate centrifugal forces to 372,000g. The pressure, P, in the sample cell is given by the relationship, $P = \rho\omega^2(X^2 - X_m^2)/2$ where $\rho$ is the density of the solution in g/cm$^3$, $\omega$ is the angular velocity in radians/sec., X is the distance from the rotor axis to the point of measurement in cm, $X_m$ is the distance from the rotor axis to the meniscus in cm, and the pressure is in dynes/cm$^2$ with 1 atm taken as $1.01 \times 10^6$ dynes/cm$^2$ (13, 14). The rotor was equipped with a cell having windows through which ultraviolet light can pass such that the cell may be scanned from top to bottom.

The rotor containing the same was equilibrated at a temperature several degrees below that of the inverse temperature transition when placed in the ultracentrifuge which was also equilibrated at the same temperature. The rotor was spun at a constant speed, and the temperature was raised at a slow rate of 0.1° C./6 min in order to maintain equilibration. The cell was scanned every six minutes using a 2 min scan time. Below the transition temperature, the optical density due to the polypentapeptide at a concentration of 40 mg/ml ($\downarrow$ 0.1M) was typically near 0.2 at 330 nm. The scans were repeated until a transition was observed initially as an increased optical density to greater than one due to light scattering as aggregates developed throughout the solution within the cell; then with settling of the aggregates, the OD went above one starting at the interface between the equilibrium solution and the coacervate phase near the bottom of the cell. The studies were carried out at 2000, 20,000 and 40,000 rpm which correspond to pressures on the samples of 1.29, 29.7, and 115 atm, respectively.

RESULTS

The data are plotted in FIG. 1 as the change in the temperature of the transition, $\Delta T_t$, versus log P. This means of linearizing the experimental results, utilizes the Clapeyron-Clausius equation, $dP/dT = L/T\Delta V$ where P is pressure, L is the latent heat of the phase change, and $\Delta V$ is the difference in volume of the phases (15, 16, 17). Since for the latent heat of the phase change at equilibrium, $L = T_t\Delta S$, where $T_t$ is the temperature of the transition, then $dP/dT = \Delta S/\Delta V$. Now dividing by P gives $d(\ln P)/dT = \Delta S/P\Delta V$ such that a slope of a $\Delta T_t$ vs. log P plot becomes $P\Delta V/\Delta S$.

The experimental $\Delta T_t$ for poly[0.857(GVGVP), 0.143(GWGVP)] in FIG. 1 was multiplied by 0.2/0.143 before plotting in order to provide a better comparison of the effects of pressure on the three aromatic residue containing polymers having similar amounts of substitution. This is reasonable as plots of $T_t$ vs. $f_x$ for different substitutions at the $Val^4$ residue are linear; a hydrophobicity scale is being developed on this basis (18). The data for poly(GMGVP) and poly(GVGVP) are for $f_x = 1$ such that a comparison of the pressure effects between these two homopolypeptides and the aromatic residue containing polypentapeptides should be divided by five. This makes even more dramatic the pressure effect introduced by the aromatic substitutions. To show this comparison, plots of the data are given assuming the linearity between and $\Delta T_t$, at 115 atm (FIG. 2, panel A) and a 30 atm (FIG. 2, panel B).

Given the Clapeyron-Clausius equation for such a phase transition (15), it becomes possible with an experimental value for the heat of the transition to estimate the change in volume. The heats of the transitions for these polypentapeptides have been determined in a sealed differential scanning calorimeter cell where the pressure is assumed to be one atmosphere. Using these values for the heats of the transition (18) and the slopes given in FIG. 1, the calculated changes in volume, $\Delta V$, attending the phase change are: 83 cm$^3$/mole-pentamer for poly[0.8(GVGVP,0.2(GFGVP)]; 61 cm$^3$/mole-pentamer for poly[0.857(GVGVP),0.143(GWGVP)]; 51 cm$^3$/mole-pentamer for poly[0.8(GVGVP),0.2-(GYGVP)]; and 3 cm$^3$/mole-pentamer for poly(GVGVP). On extrapolating to $f_x = 1$, the comparison becomes 420, 430, 260 and 3 cm$^3$/mole-pentamer, respectively, that is, the volume changes for the pure pentamer would be seven times larger, for poly(GWGVP), i.e., the volume change would be 430 cm$^3$/mole-pentamer. Experimental data could not be obtained directly on the homopolypentapeptides poly(GWGVP), poly(GFGVP) and poly(GYGVP) using this technique, because these are insoluble in water due to transition temperatures that are well below 0° C. The extrapolated values of $T_t$ for these homopolypentapeptides are $-100°$ C., $-45°$ C. and $-70°$ C., respectively (18), as derived from FIG. 4.

All publications and patent applications mentioned in this specification are herein incorporated by reference to the same extent as if each individual publication or patent application was specifically and individually indicated to be incorporated by reference at the location where cited.

The invention now being fully described, it will be apparent to one of ordinary skill in the art that many changes and modifications can be made thereto without departing from the spirit or scope of the appended claims.

What is claimed is:

1. A method of producing mechanical work, which comprises:
   changing pressure on a bioelastic polymer containing elastomeric units selected from the group consisting of bioelastic pentapeptides, tetrapeptides, and nonapeptides, wherein at least a fraction of said elastomeric units contain at least one amino acid residue with a hydrophobic side chain that is at least as large as 20 $cm^3$/mole and which is present in an amount sufficient to provide PdV/dS for said polymer of at least 0.2° K., wherein said polymer is constrained so that expansion or contraction of said polymer produces mechanical work.

2. The method of claim 1, wherein said polymer is present in a fluid-containing environment and said pressure is changed by increasing the pressure that said fluid exerts on said polymer.

3. The method of claim 1, wherein said polymer is present in a fluid-containing environment and said pressure is changed by reducing the pressure that said fluid exerts on said polymer.

4. The method of claim 1, wherein said pressure is reduced, whereby an object in contact with said polymer which is under the influence of a force resisted by said polymer moves under the influence of said force as said polymer contracts.

5. An apparatus for producing mechanical work, which comprises:
   a bioelastic polymer containing elastomeric units selected from the group consisting of bioelastic pentapeptides, tetrapeptides, and nonapeptides, wherein at least a fraction of said elastomeric units contain at least one amino acid residue with a hydrophobic side chain that is at least as large as 20 $cm^3$/mole and which is present in an amount sufficient to provide PdV/dS for said polymer of at least 0.2° K.;
   means for constraining said polymer wherein expansion of said polymer will produce mechanical work; and
   means for applying pressure to said polymer, whereby increasing said pressure causes said polymer to expand and produce said mechanical work.

6. The apparatus of claim 5, wherein said means for constraining comprises a cylinder and piston.

7. The apparatus of claim 5, wherein said means for constraining comprises a deformable sheath.

8. The apparatus of claim 7, wherein deformation of said sheath by expansion of said polymer acts to move an object contacting said sheath through a distance against an opposing force.

* * * * *